(12) United States Patent
Blanchard et al.

(10) Patent No.: US 9,044,541 B2
(45) Date of Patent: Jun. 2, 2015

(54) PRESSURE ACTIVATED PROXIMAL VALVES

(75) Inventors: Daniel B. Blanchard, Bountiful, UT (US); Kelly B. Powers, North Salt Lake, UT (US); William R. Barron, Riverton, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 1903 days.

(21) Appl. No.: 11/566,620

(22) Filed: Dec. 4, 2006

(65) Prior Publication Data
US 2007/0161940 A1 Jul. 12, 2007

Related U.S. Application Data

(60) Provisional application No. 60/741,578, filed on Dec. 2, 2005.

(51) Int. Cl.
| | |
|---|---|
| *A61M 5/00* | (2006.01) |
| *A61M 5/168* | (2006.01) |
| *A61M 25/00* | (2006.01) |
| *A61M 39/22* | (2006.01) |
| *F16K 15/14* | (2006.01) |
| *A61M 25/06* | (2006.01) |

(52) U.S. Cl.
CPC ....... *A61M 5/16881* (2013.01); *A61M 25/0075* (2013.01); *A61M 25/0693* (2013.01); *A61M 39/22* (2013.01); *F16K 15/147* (2013.01)

(58) Field of Classification Search
CPC ............... A61M 25/0075; A61M 25/0693; A61M 39/22; A61M 5/16881; F04B 3/00; F04B 53/006; F04B 53/103; F16K 15/147
USPC .......... 604/6.1, 167.04, 30, 247, 256, 167.01, 604/167.03, 246, 31, 533, 537, 905; 137/843, 844, 846, 847, 849
See application file for complete search history.

(56) References Cited

U.S. PATENT DOCUMENTS

| | | | |
|---|---|---|---|
| 274,447 A | * | 3/1883 | Kennish .................... 251/143 |
| 856,270 A | | 6/1907 | Lewis |
| 966,137 A | | 8/1910 | Storey et al. |

(Continued)

FOREIGN PATENT DOCUMENTS

| | | |
|---|---|---|
| CA | 1052659 | 4/1979 |
| DE | 03326696 | 6/1984 |

(Continued)

OTHER PUBLICATIONS

CN 200680042508.1 filed Dec. 4, 2006 Office Action dated Apr. 6, 2010.

(Continued)

*Primary Examiner* — Kevin C Sirmons
*Assistant Examiner* — Imani Hayman
(74) *Attorney, Agent, or Firm* — Rutan & Tucker, LLP

(57) ABSTRACT

A medical device is disclosed comprising a diaphragm having at least one slit valve disposed therein, and a valve housing configured to secure the diaphragm at a peripheral portion of the diaphragm, wherein a central portion of the diaphragm is positioned relative to the peripheral portion of the diaphragm such that compressive forces acting on the peripheral portion of the diaphragm create moment forces which bias the slit valve in a closed position. A method is disclosed for using the device in connection with a catheter for regulation of fluids to and from a patient.

20 Claims, 11 Drawing Sheets

(56) References Cited

U.S. PATENT DOCUMENTS

| | | | |
|---|---|---|---|
| 2,629,393 A | 2/1953 | Langdon | |
| 2,896,661 A | 7/1959 | Becker | |
| 2,941,544 A | 6/1960 | Peras | 137/844 |
| 3,007,527 A | 11/1961 | Nelson | 166/326 |
| 3,151,626 A | 10/1964 | Everett | |
| 3,155,110 A | 11/1964 | Hoffman | |
| 3,176,712 A | 4/1965 | Ramsden | 137/496 |
| 3,245,428 A | 4/1966 | Klimak | 137/493 |
| 3,275,291 A | 9/1966 | Meijers | 251/331 |
| 3,298,391 A | 1/1967 | Savage | 137/493 |
| 3,504,669 A | 4/1970 | Albert | |
| 3,566,913 A | 3/1971 | Parthe, Jr. | |
| 3,620,500 A | 11/1971 | Santomieri | 251/149.1 |
| 3,717,177 A | 2/1973 | Glesmann | 137/607 |
| 3,759,249 A | 9/1973 | Fletcher et al. | 600/532 |
| 3,770,009 A | 11/1973 | Miller | 137/543.19 |
| 3,811,466 A | 5/1974 | Ohringer | 137/493 |
| 3,822,720 A | 7/1974 | Souza | |
| 3,848,579 A | 11/1974 | Villa-Real | 600/577 |
| 3,861,412 A | 1/1975 | Fleischmann | 137/83 |
| 3,897,682 A | 8/1975 | Brooks | 73/149 |
| 3,906,930 A | 9/1975 | Guerra | 600/579 |
| 3,941,149 A | 3/1976 | Mittleman | 137/493.1 |
| 3,960,142 A | 6/1976 | Elliott et al. | 600/538 |
| 3,991,768 A | 11/1976 | Portnoy | 604/10 |
| 3,996,923 A | 12/1976 | Guerra | 600/579 |
| 4,003,398 A | 1/1977 | Duveau | 137/512 |
| 4,044,763 A | 8/1977 | Bird | 128/204.26 |
| 4,103,686 A | 8/1978 | LeFevre | 604/249 |
| 4,127,123 A | 11/1978 | Bird | 128/204.25 |
| 4,134,424 A | 1/1979 | Zeyra et al. | |
| 4,143,853 A | 3/1979 | Abramson | 251/149.1 |
| 4,197,735 A | 4/1980 | Munzer et al. | 73/61.68 |
| 4,244,379 A | 1/1981 | Smith | 128/766 |
| 4,341,239 A | 7/1982 | Atkinson | 137/493 |
| 4,342,315 A | 8/1982 | Jackson | 604/35 |
| 4,367,767 A | 1/1983 | Hurd | 137/489 |
| 4,387,879 A | 6/1983 | Tauschinski | 251/149.1 |
| 4,401,116 A | 8/1983 | Fry et al. | 128/205.24 |
| 4,417,567 A | 11/1983 | Trick | 600/31 |
| 4,430,081 A | 2/1984 | Timmermans | 604/256 |
| 4,434,810 A * | 3/1984 | Atkinson | 137/493 |
| 4,436,519 A | 3/1984 | O'Neill | |
| 4,439,182 A | 3/1984 | Huang | 604/85 |
| 4,470,412 A | 9/1984 | Nowacki et al. | 128/200.18 |
| 4,475,898 A | 10/1984 | Brodner et al. | 604/9 |
| 4,487,207 A | 12/1984 | Fitz | 482/1 |
| 4,487,606 A | 12/1984 | Leviton et al. | 604/319 |
| 4,510,805 A | 4/1985 | Saint-Amour | 73/37.9 |
| 4,512,766 A | 4/1985 | Vailancourt | 604/167.03 |
| 4,520,819 A | 6/1985 | Birmingham et al. | 606/202 |
| 4,533,347 A | 8/1985 | Deckert | 604/81 |
| 4,535,818 A | 8/1985 | Duncan et al. | 137/846 |
| 4,535,819 A | 8/1985 | Atkinson et al. | 137/846 |
| 4,542,740 A | 9/1985 | Kleinschmidt et al. | 128/204.21 |
| 4,549,879 A | 10/1985 | Groshong et al. | 604/247 |
| 4,553,686 A | 11/1985 | Dougherty | 222/212 |
| 4,566,493 A | 1/1986 | Edwards et al. | 137/846 |
| 4,568,337 A | 2/1986 | Treharne, III et al. | 604/247 |
| 4,576,035 A | 3/1986 | Hooven et al. | 73/1.59 |
| 4,608,042 A | 8/1986 | Vanderveen et al. | 604/81 |
| 4,610,275 A | 9/1986 | Beecher | 137/854 |
| 4,610,469 A | 9/1986 | Wolff-Mooij | 285/260 |
| 4,626,245 A | 12/1986 | Weinstein | 604/167.04 |
| 4,634,027 A | 1/1987 | Kanarvogel | 222/380 |
| 4,640,277 A | 2/1987 | Meyer et al. | 128/204.23 |
| 4,651,730 A | 3/1987 | von dem Hagen et al. | 128/204.21 |
| 4,671,796 A | 6/1987 | Groshong et al. | 604/247 |
| 4,673,393 A | 6/1987 | Suzuki et al. | 604/167.04 |
| 4,674,526 A | 6/1987 | Athanassiu | 137/113 |
| 4,698,075 A | 10/1987 | Dechene | 96/116 |
| 4,701,166 A | 10/1987 | Groshong et al. | 604/247 |
| 4,713,054 A | 12/1987 | Kelly et al. | 604/89 |
| 4,722,725 A | 2/1988 | Sawyer | 604/27 |
| 4,752,287 A | 6/1988 | Kurtz et al. | 604/99.02 |
| 4,769,017 A | 9/1988 | Fath et al. | 604/533 |
| 4,770,170 A | 9/1988 | Sato et al. | 128/207.15 |
| 4,784,175 A | 11/1988 | Hicks | 137/202 |
| 4,838,261 A | 6/1989 | von dem Hagen | 128/205.24 |
| 4,865,583 A | 9/1989 | Tu | 604/508 |
| 4,867,741 A | 9/1989 | Portnoy | 604/10 |
| 4,895,565 A | 1/1990 | Hillstead | |
| 4,904,245 A | 2/1990 | Chen et al. | 604/248 |
| 4,930,535 A | 6/1990 | Rinehold | 137/15.18 |
| 4,932,633 A | 6/1990 | Johnson et al. | |
| 4,946,448 A | 8/1990 | Richmond | 604/247 |
| 4,949,448 A | 8/1990 | Hebnes | |
| 4,960,412 A | 10/1990 | Fink | 604/167.04 |
| 4,966,137 A | 10/1990 | Davini | |
| 4,968,294 A | 11/1990 | Salama | |
| 4,972,929 A | 11/1990 | Ivers et al. | |
| 4,973,319 A | 11/1990 | Melsky | 604/247 |
| 4,995,863 A | 2/1991 | Nichols et al. | 604/247 |
| 5,000,745 A | 3/1991 | Guest et al. | 604/256 |
| 5,025,829 A | 6/1991 | Edwards et al. | 137/512 |
| 5,030,210 A | 7/1991 | Alchas | 604/247 |
| 5,038,621 A | 8/1991 | Stupecky | 73/861.53 |
| 5,041,095 A | 8/1991 | Littrell | 604/167.04 |
| 5,062,448 A | 11/1991 | Hilsenbeck | 137/498 |
| 5,064,416 A | 11/1991 | Newgard | 604/167.03 |
| 5,071,411 A | 12/1991 | Hillstead et al. | 604/246 |
| 5,085,635 A | 2/1992 | Cragg | 604/102.03 |
| 5,098,393 A | 3/1992 | Amplatz et al. | |
| 5,113,911 A | 5/1992 | Hirsh | 137/844 |
| 5,125,903 A | 6/1992 | McLaughlin et al. | |
| 5,135,489 A | 8/1992 | Jepson et al. | 604/48 |
| 5,141,029 A | 8/1992 | Naugle et al. | 138/44 |
| 5,141,498 A | 8/1992 | Christian | 604/167.03 |
| 5,147,313 A | 9/1992 | Dikeman | 604/153 |
| 5,147,332 A | 9/1992 | Moorehead | 604/247 |
| 5,149,327 A | 9/1992 | Oshiyama | 604/167.04 |
| 5,154,701 A | 10/1992 | Cheer et al. | |
| 5,156,600 A | 10/1992 | Young | 604/247 |
| 5,160,325 A | 11/1992 | Nichols et al. | 604/247 |
| 5,167,615 A | 12/1992 | East et al. | 604/9 |
| 5,167,637 A | 12/1992 | Okada et al. | 604/167.04 |
| 5,169,393 A | 12/1992 | Moorehead et al. | 604/247 |
| 5,176,652 A | 1/1993 | Littrell | |
| 5,201,722 A | 4/1993 | Moorehead et al. | 604/247 |
| 5,201,725 A | 4/1993 | Kling | 604/284 |
| 5,205,834 A | 4/1993 | Moorehead et al. | 604/247 |
| 5,224,938 A | 7/1993 | Fenton, Jr. | 604/247 |
| 5,249,598 A * | 10/1993 | Schmidt | 137/493.1 |
| 5,261,459 A | 11/1993 | Atkinson et al. | |
| 5,269,763 A | 12/1993 | Boehmer et al. | |
| 5,279,587 A | 1/1994 | Weenig | 604/247 |
| 5,290,263 A | 3/1994 | Wigness et al. | 604/247 |
| 5,295,658 A | 3/1994 | Atkinson et al. | 251/149.1 |
| 5,301,707 A | 4/1994 | Hofsteenge | 137/12 |
| 5,312,363 A | 5/1994 | Ryan et al. | |
| 5,396,925 A | 3/1995 | Poli | 137/493 |
| 5,402,982 A | 4/1995 | Atkinson et al. | |
| 5,409,463 A | 4/1995 | Thomas et al. | |
| 5,411,491 A | 5/1995 | Goldhardt et al. | |
| 5,453,097 A | 9/1995 | Paradis | 604/247 |
| 5,549,565 A | 8/1996 | Ryan et al. | |
| 5,660,200 A | 8/1997 | Paes | 137/110 |
| 5,727,594 A | 3/1998 | Choksi | 137/859 |
| 5,730,336 A * | 3/1998 | Lerner | 222/490 |
| 5,771,935 A | 6/1998 | Myers | |
| 5,784,999 A * | 7/1998 | Larson et al. | 119/71 |
| 5,800,339 A | 9/1998 | Salama | 600/29 |
| 5,807,349 A | 9/1998 | Person et al. | |
| 5,833,671 A | 11/1998 | Macoviak et al. | 604/247 |
| 5,843,044 A | 12/1998 | Moorehead | 604/247 |
| 5,853,397 A | 12/1998 | Shemesh et al. | 604/247 |
| 5,858,007 A | 1/1999 | Fagan et al. | |
| 5,984,902 A | 11/1999 | Moorehead | 604/247 |
| 6,024,729 A | 2/2000 | Dehdashtian et al. | 604/256 |
| 6,059,757 A | 5/2000 | Macoviak et al. | |
| 6,322,541 B2 | 11/2001 | West et al. | |
| 6,428,520 B1 | 8/2002 | Lopez et al. | |
| 6,530,504 B2 * | 3/2003 | Socier | 222/494 |

(56) References Cited

U.S. PATENT DOCUMENTS

| | | | |
|---|---|---|---|
| 6,632,200 | B2 | 10/2003 | Potter et al. |
| 6,923,822 | B2 | 8/2005 | Crawford et al. |
| 7,004,931 | B2 | 2/2006 | Hogendijk |
| 7,037,303 | B2 | 5/2006 | Beaufore et al. |
| 7,044,150 | B2 | 5/2006 | Seidl |
| 7,252,652 | B2 | 8/2007 | Moorehead et al. ......... 604/247 |
| 7,435,236 | B2 | 10/2008 | Weaver et al. |
| 7,491,192 | B2 | 2/2009 | DiFiore |
| 7,540,851 | B2 | 6/2009 | O'Mahony et al. |
| 7,601,141 | B2 | 10/2009 | Dikeman et al. |
| 2002/0010425 | A1 | 1/2002 | Guo et al. |
| 2002/0010488 | A1 | 1/2002 | Crawford et al. |
| 2002/0026139 | A1 | 2/2002 | Bertrand et al. |
| 2002/0156430 | A1 | 10/2002 | Haarala et al. ............... 604/247 |
| 2003/0111122 | A1* | 6/2003 | Horton .......................... 137/846 |
| 2004/0003846 | A1 | 1/2004 | Seidl |
| 2004/0102738 | A1 | 5/2004 | Dikeman et al. ............. 604/256 |
| 2004/0144435 | A1 | 7/2004 | Dark |
| 2004/0176743 | A1 | 9/2004 | Morris et al. ................. 604/537 |
| 2004/0186444 | A1 | 9/2004 | Daly et al. .................... 604/247 |
| 2004/0193118 | A1 | 9/2004 | Bergeron ...................... 604/247 |
| 2004/0193119 | A1 | 9/2004 | Canaud et al. ............... 604/247 |
| 2005/0027261 | A1* | 2/2005 | Weaver et al. ............... 604/246 |
| 2005/0049555 | A1 | 3/2005 | Moorehead et al. |
| 2005/0171488 | A1 | 8/2005 | Weaver et al. |
| 2005/0171489 | A1 | 8/2005 | Weaver et al. |
| 2005/0171490 | A1 | 8/2005 | Weaver et al. |
| 2005/0171510 | A1 | 8/2005 | DiCarlo et al. |
| 2005/0257837 | A1 | 11/2005 | Bailey |
| 2005/0261725 | A1 | 11/2005 | Crawford et al. |
| 2005/0267487 | A1 | 12/2005 | Christensen et al. |
| 2006/0037975 | A1* | 2/2006 | Suffa ............................ 222/490 |
| 2006/0145116 | A1 | 7/2006 | Rickerd et al. |
| 2006/0149214 | A1 | 7/2006 | Breiter et al. |
| 2006/0212003 | A1 | 9/2006 | Fangrow, Jr. ................. 604/247 |
| 2006/0224127 | A1 | 10/2006 | Fangrow, Jr. ................. 604/247 |
| 2006/0276751 | A1 | 12/2006 | Haberland et al. |
| 2007/0233007 | A1 | 10/2007 | Adams ...................... 604/168.01 |
| 2009/0043261 | A1 | 2/2009 | Weaver et al. |
| 2009/0177187 | A1 | 7/2009 | Quigley et al. |
| 2010/0036328 | A1 | 2/2010 | Dikeman et al. |

FOREIGN PATENT DOCUMENTS

| | | |
|---|---|---|
| EP | 85308118 | 11/1985 |
| EP | 89311584 | 11/1989 |
| EP | 1954343 A2 | 8/2008 |
| GB | 966137 A | 8/1964 |
| GB | 2217433 | 12/1988 |
| JP | 52118356 A | 10/1977 |
| JP | 52118357 A | 10/1977 |
| JP | 54-52312 | 4/1979 |
| JP | 54-52313 | 4/1979 |
| JP | 61155410 A | 7/1986 |
| JP | 63-11817 | 1/1988 |
| JP | 01034840 | 2/1989 |
| JP | 2-213354 | 8/1990 |
| WO | WO8000923 | 11/1979 |
| WO | WO8300049 | 6/1982 |
| WO | WO8403838 | 3/1984 |

OTHER PUBLICATIONS

CN 200680042508.1 filed Dec. 4, 2006 Office Action dated Sep. 18, 2009.
EP 0683819.6 filed Dec. 4, 2006 Office Action dated Apr. 14, 2010.
EP 0683819.6 filed Dec. 4, 2006 Office Action dated May 6, 2009.
PCT/US2006/046216 filed Dec. 4, 2006 International Preliminary Report on Patentability dated Jun. 4, 2008.
PCT/US2006/046216 filed Dec. 4, 2006 Search Report dated Jun. 6, 2007.
PCT/US2006/046216 filed Dec. 4, 2006 Written Opinion dated Jun. 6, 2007.
Uchiyama, Manabu et al, Nonlinear Buckling Simulations of Imperfect Shell Domes using a Hybrid Finite Element Formulation and the Agreement with Experiments, Fourth International Colloquium on Computation of Shell & Spatial Structures, 14 pages, Chania-Crete, Greece, Jun. 5-7, 2000.
Zhiming, Ye, Nonlinear Analysis and Optimization of Shallow Shells of Variable Thickness, printed from http://www.shu.edu.cn/journal/vol1no2199705.htm.
CA 2,626,335 filed Dec 4, 2006 Examiner's Report dated Aug. 13, 2012.
CN 200680042508.1 filed Dec. 4, 2006 Office Action dated Mar. 29, 2012.

* cited by examiner

PRESSURE ACTIVATED PROXIMAL VALVES

CROSS-REFERENCE TO RELATED APPLICATION

This application claims the benefit of U.S. Provisional Application No. 60/741,578, entitled "PRESSURE-ACTIVATED PROXIMAL VALVES," filed Dec. 2, 2005, which is incorporated herein by reference in its entirety.

BACKGROUND

In medicine, an embolism occurs when an object (the embolus, plural emboli) migrates from one part of the body (through circulation) and causes a blockage of a blood vessel in another part of the body. Blood clots form a common embolic material. Other possible embolic materials include fat globules (a fat embolism), air bubbles (an air embolism), septic emboli (containing pus and bacteria), or amniotic fluid. Emboli often have more serious consequences when they occur in the so-called "end-circulation" areas of the body that have no redundant blood supply, such as the brain, heart, and lungs. Assuming normal circulation, a thrombus or other embolus formed in a systemic vein will always impact in the lungs, after passing through the right side of the heart. This forms a pulmonary embolism that can be a complication of deep-vein thrombosis.

Embolism can be contrasted with a "thrombus" which is the formation of a clot within a blood vessel, rather than being carried from elsewhere. Thrombus, or blood clot, is the final product of the blood coagulation step in hemostasis. It is achieved via the aggregation of platelets that form a platelet plug, and the activation of the humoral coagulation system (i.e., clotting factors). A thrombus is physiologic in cases of injury, but pathologic in case of thrombosis. A thrombus in a large blood vessel will decrease blood flow through that vessel. In a small blood vessel, blood flow may be completely cut-off resulting in the death of tissue supplied by that vessel. If a thrombus dislodges and becomes free-floating, it becomes an embolus.

Some of the conditions in which blood clots develop include atrial fibrillation (a form of cardiac arrhythmia), heart valve replacement, a recent heart attack, extended periods of inactivity (see deep venous thrombosis), and genetic or disease-related deficiencies in the blood's clotting abilities.

Preventing blood clots reduces the risk of stroke, heart attack and pulmonary embolism. Heparin and warfarin are often used to inhibit the formation and growth of existing blood clots, thereby allowing the body to shrink and dissolve the blood clots through normal methods (see anticoagulant). Regulating fluid flow through catheters can help minimize embolism and health risks associated therewith.

BRIEF SUMMARY

One aspect of the present invention discloses a medical device comprising a diaphragm having at least one slit valve disposed therein and at least one valve control member. The term "diaphragm," as used herein, can be defined as any membranous part that divides or separates. The valve control member can be configured to cover at least a portion of the diaphragm without covering any portion of the slit valve and can be further configured to control deflection of the diaphragm. In another aspect of the invention, the valve control member comprises at least one arm extending from an outer portion of the valve control member to an inner portion of the valve control member. In still another aspect of the invention, the valve control member comprises a plurality of arms extending from an outer portion of the valve control member to a center portion of the valve control member. Further, the medical device can comprise a valve housing having the diaphragm therein, the valve housing being configured to be attached to an elongated tubular member, the elongated tubular member configured for at least partial placement into a portion of a patient. In another aspect of the invention, at least a portion of the slit valve has a nonlinear orientation. In another aspect of the invention the slit valve further comprises a plurality of interconnected linear slits oriented in different directions.

In another embodiment, a medical device for regulating fluid flow comprises a diaphragm having a slit valve disposed therein and a valve housing configured to secure the diaphragm at a peripheral portion of the diaphragm. A distal end of the valve housing can be further configured to attach to a proximal end of an elongated tubular member, such as a catheter. A central portion of the diaphragm is positioned relative to the peripheral portion of the diaphragm such that compressive forces acting on the peripheral portion of the diaphragm create moment forces which bias the slit valve in a neutral position. In one aspect of the invention, an outer portion of the diaphragm is thicker than an inner portion of the diaphragm. Alternatively, in another aspect of the invention, an outer portion of the diaphragm is thinner than an inner portion of the diaphragm. In still another aspect of the invention, the diaphragm may be substantially circular or substantially oval. In an additional embodiment of the invention, at least a portion of the diaphragm approximates the shape of a dome structure. In one aspect, the diaphragm further comprises a concave or convex annular member which circumscribes the dome structure. In one embodiment, the diaphragm is oriented substantially perpendicular to a direction of flow through the valve housing. In another embodiment, the diaphragm is oriented at an obtuse angle relative to a direction of flow through the valve housing. In one aspect, the diaphragm narrows from a lateral portion of the diaphragm to an opposite lateral portion of the diaphragm. In still another aspect, at least two slit valves are installed on opposing sides of the diaphragm.

In another embodiment, the diaphragm of the medical device further comprises at least one protruding member on a proximal end of the diaphragm configured to assist the slit valve to return to the biased neutral position. In one aspect, the diaphragm further comprises a pair of centrally located opposing protruding members on a proximal end of the diaphragm configured to assist the slit valve to return to the biased neutral position.

One embodiment of the invention contemplates a medical device comprising a diaphragm with at least one slit valve disposed therein. The proximal surface and distal surface of the diaphragm approximate a dome structure. The diaphragm is configured such that a portion of the proximal end of the diaphragm contiguous with the slit valve is thinner than an adjacent portion of the diaphragm. In one aspect, the diaphragm is secured at a peripheral portion by a valve housing, a distal end of the valve housing being configured to attach to a proximal portion of an elongated tubular member. In another aspect, the height of the peripheral portion of the diaphragm is greater than the height of the dome structure of the diaphragm at the apex of the dome structure of the diaphragm. In yet another aspect, the height of the peripheral portion of the diaphragm is approximately twice the width of the peripheral portion of the diaphragm. In another embodiment, the peripheral portion of the diaphragm is compressed by the valve housing approximately five to 15 percent. In another embodiment, a central portion of the diaphragm is subjected to moment forces from compression of the peripheral portion of the diaphragm thereby biasing the slit valve in a neutral position. In still another embodiment, a central portion of the diaphragm is positioned at a proximal end of the peripheral portion of the diaphragm.

In another embodiment of the present invention, a medical device comprises a cylindrical member having a proximal end configured to be secured at a peripheral portion by a valve housing, wherein the peripheral portion has a circumference greater than the circumference of the main cylindrical member. The medical device further comprises at least one slit valve placed on an outer wall of the cylindrical member. The slit valve is oriented parallel to a longitudinal axis of the cylindrical member. In one aspect, a distal end of the valve housing is configured to attach to a proximal end of an elongated tubular member, wherein a distal portion of the elongated tubular member is configured to be placed within a portion of a patient.

In a further embodiment, a medical device comprises a pressure-activated valve having an open circular proximal end and an at least partially closed distal end. The medical device is further configured such that the distal end comprises at least a partially planar surface having at least two slits oriented in different directions disposed therein. The slits have at least one common intersection and are configured to actuate in a distal direction in response to a first pressure differential. The medical device is further configured such that a portion of the distal end of the valve is defined by an interior angle of the intersecting slits, an outer portion of the distal end of the valve tapering from the distal end of the valve towards the proximal end of the valve thereby forming a channel on the outer portion of the distal end of the valve. In one aspect, the medical device further comprises at least one proximal-actuating slit valve installed on the distal end. The slit valve is configured to actuate in a proximal direction in response to a second pressure differential. In this aspect, the second pressure differential is greater than the first pressure differential. In another aspect, the slits placed in the distal end of the valve are oriented to approximate the shape of a cruciform thereby separating the distal end of the valve into quadrants. In one aspect, the valve is further configured such that the center of the cruciform is approximately collinear with the center of the circular proximal end of the valve. In yet another aspect, the at least one proximal-actuating slit valve is placed in a bottom portion of the channel.

In an additional embodiment, a method is disclosed comprising the steps of placing a distal end of a catheter into a vasculature of a patient, wherein a proximal end of the catheter has a medical device connected thereto. The medical device comprises a diaphragm having at least one slit valve disposed therein and a valve housing configured to secure the diaphragm at a peripheral portion of the diaphragm. A central portion of the diaphragm is positioned relative to the peripheral portion of the diaphragm such that compressive forces acting on the peripheral portion of the diaphragm create moment forces which bias the slit valve in a neutral position. The method further comprises the steps of creating a first liquid pressure differential across the slit valve thereby infusing liquids into the patient and creating a second pressure differential across the slit valve thereby aspirating liquids from a patient.

Features from any of the above-mentioned embodiments may be used in combination with one another in accordance with the instant disclosure. In addition, other features and advantages of the instant disclosure will become apparent to those of ordinary skill in the art through consideration of the ensuing description, the accompanying drawings, and the appended claims.

BRIEF DESCRIPTION OF THE DRAWINGS

Advantages of the present invention will become apparent upon review of the following detailed description and drawings, which illustrate representations (not necessarily drawn to scale) of various embodiments of the invention, wherein.

DETAILED DESCRIPTION

One aspect of the instant disclosure relates to apparatuses and systems for pressure-activated valves for use with a medical device. Specifically, the instant disclosure contemplates that a slit valve may be disposed within a medical device, such as a catheter, for selective infusion and aspiration of fluids through the catheter and into a patient.

Figure 1:
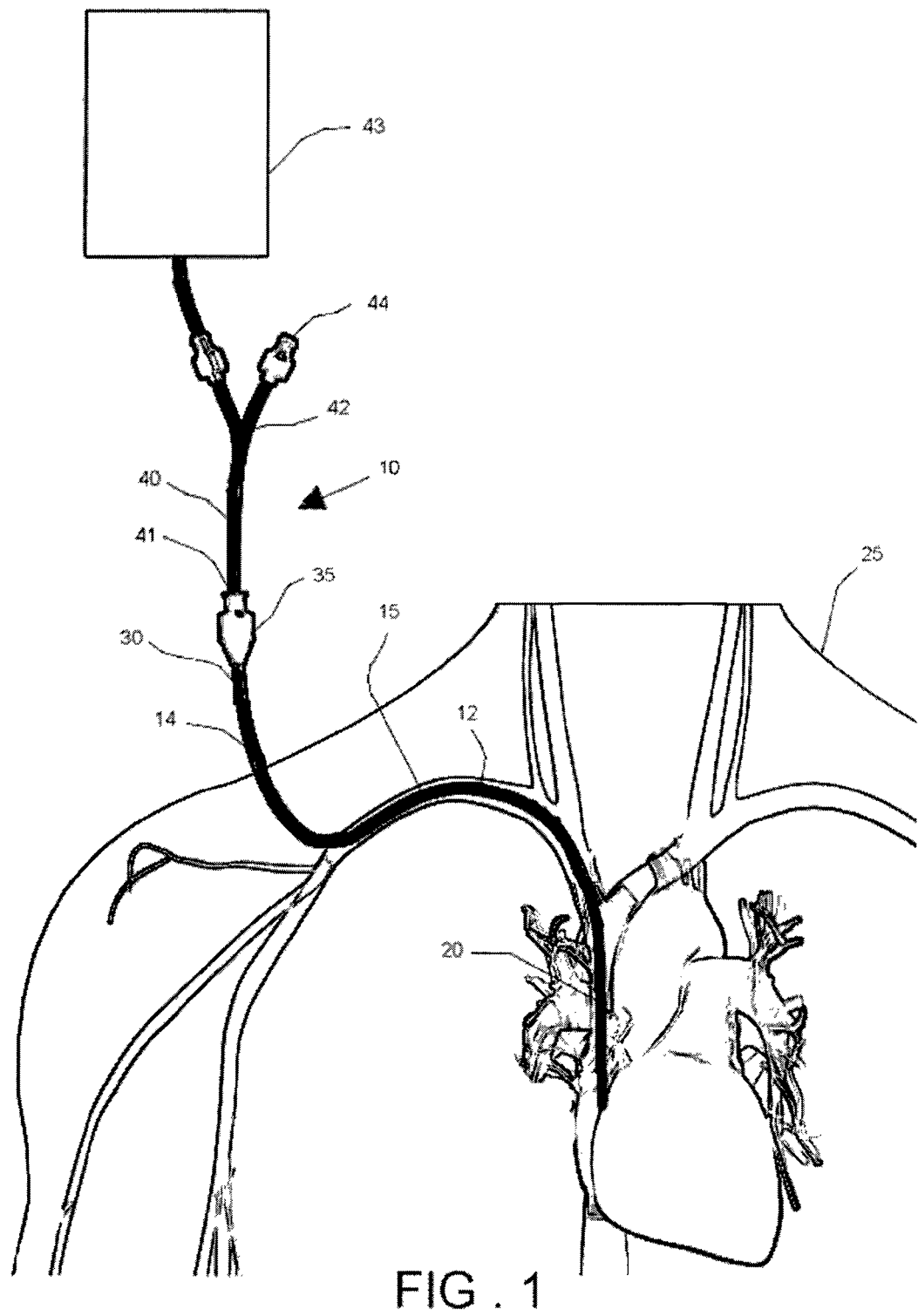
FIG. 1 is a front view of a patient with a catheter assembly placed within a vasculature of the patient.
Figure 2:
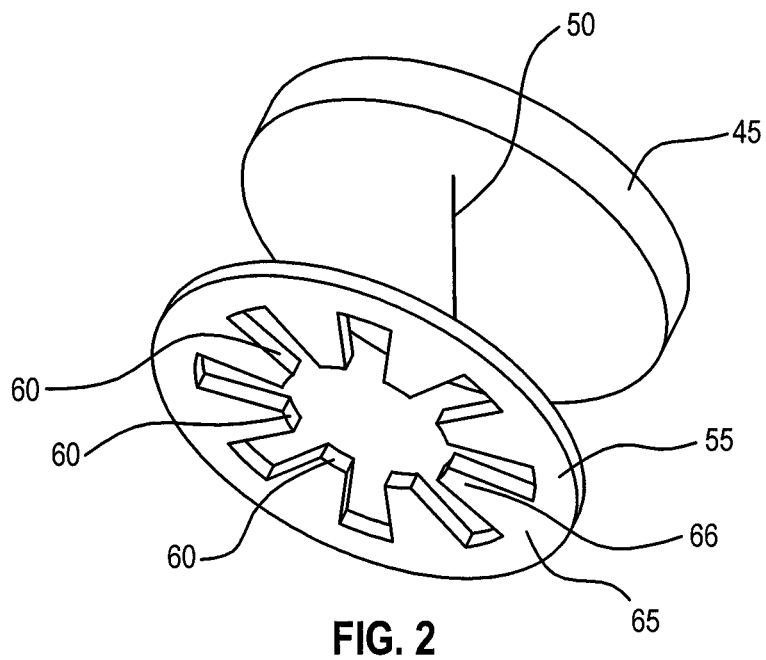
FIG. 2 is a perspective view of a diaphragm with a slit valve disposed therein and a valve control member.
Figure 3:
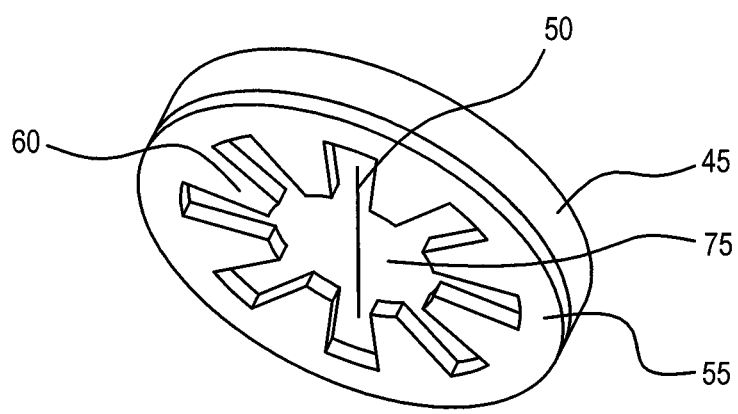
FIG. 3 is a perspective view of the diaphragm and valve control member of FIG. 2 adjacent one another.
Figure 4:
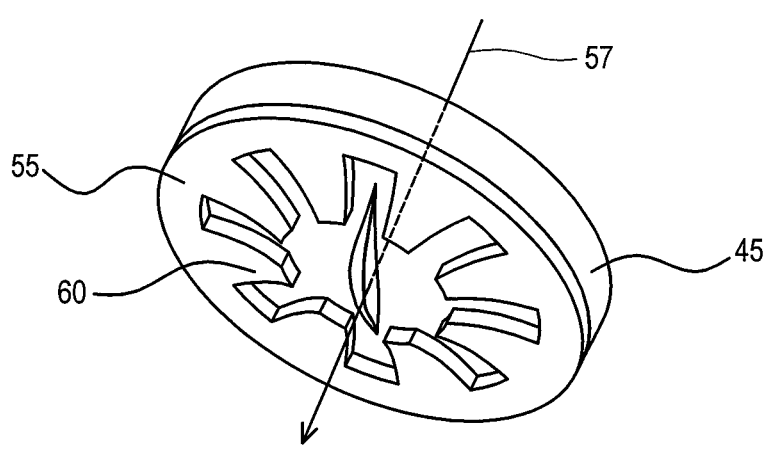
FIG. 4 is a perspective of the diaphragm and valve control member of FIG. 3 illustrating actuation of the valve in a distal direction.

Referring to FIG. 1, catheter assembly 10 may be of any type that can be disposed within a body cavity, duct, or vessel. Examples of such catheters include, without limitation, peripherally inserted central catheters, central venous catheters, intravenous catheters, urological catheters, as well as catheters utilized for ventilation, pleural drainage, angioplasty, or enteral feeding. FIG. 1 illustrates a catheter 14 peripherally placed via a subclavian vein 12. However, catheter 14 can be disposed within any portion of a patient wherein drainage, injection or aspiration of fluids, access by surgical instruments, etc. is desired. Catheter 14 comprises a first portion 15 having distal end 20 configured for placement into a portion of a patient 25 and a proximal end 30 configured for attachment to a valve assembly 35. Catheter assembly 10 further comprises a second portion 40 having a distal end 41 configured for attachment to valve assembly 35 and a proximal end 42 configured for attachment to a fluid source 43 and a fluid removal and fluid injection location 44.

In one embodiment, fluid may be delivered via catheter assembly 10 to patient 25 via an IV bag connected to a proximal portion of the catheter assembly 10 wherein the fluid is substantially gravity-fed to the patient 25. In another embodiment, fluids may be power injected via the catheter assembly 10 to the patient 25 by connecting a proximal portion of the second portion 40 of the catheter assembly 10 to a power injection system. In another aspect of the invention, fluids may be aspirated by connecting a syringe to the fluid removal location 44 and applying negative pressure to the catheter assembly 10.

Generally, one aspect of the invention contemplates a pressure-activated valve positioned in the flow path of a catheter inserted into a patient. The valve can be actuated in a distal direction by a first pressure differential, for example, gravity-induced pressure from a fluid source, such as an IV bag. The valve can also be actuated in a distal direction, for example, by power injection of contrast media into the patient. The valve can also be actuated in a proximal direction by a second pressure differential, for example, by negative pressure from a syringe thereby enabling blood withdrawal from the patient. In one embodiment, the first pressure differential is less than the second pressure differential. However, any of the pressure-activated valves disclosed herein can be reversed thereby changing the pressure differential paradigm (e.g., the first pressure differential is greater than the second pressure differential).

Referring now to FIGS. 1 through 4, in one embodiment, a valve assembly 35 can include a diaphragm 45 with at least one slit valve 50 disposed therein and a valve control member 55 disposed adjacent the diaphragm 45. By itself, the slit valve 50 is configured to actuate in both a proximal direction and a distal direction in response to a proximal pressure or a distal pressure, respectively. The valve control member 55 is configured to control deflection of the diaphragm 45 in a proximal direction thereby restricting actuation of the slit valve 50 in the proximal direction 57. As a result, when the valve control member 55 is positioned adjacent the diaphragm 45, the pressure differential which actuates the slit valve 50 in a distal direction is less than the pressure differential required to actuate the slit valve 50 in a proximal direction. In one embodiment, the diaphragm 45 is circular and the valve control member 50 is correspondingly circular. However, the diaphragm 45 and valve control member 55 can be oval, rectangular, or any other suitable shape. The valve control member 55 can be placed on a distal end of the diaphragm 45, on a proximal end of the diaphragm 45, or on both ends of the diaphragm 45.

In one aspect of the invention, the valve control member 55 comprises at least one arm 60 extending from an outer portion 65 of the valve control member 55 to an inner portion 66 of the valve control member 55. In this aspect of the invention, the arm can extend laterally across a portion of the face of the diaphragm or any other angular orientation. In another embodiment, the valve control member 55 comprises a plurality of arms 60 extending from an outer portion 65 of the valve control member 55 to a center portion 66 of the valve control member 55. In one embodiment, a single slit valve 50 is disposed substantially within the center 75 of the diaphragm 45 and is substantially linear. In another embodiment several slit valves may be disposed either centrally or about the periphery of the diaphragm. Additionally, the slit valves may have a nonlinear orientation or may comprise a plurality of interconnected linear slits oriented in different directions.

Figure 5:
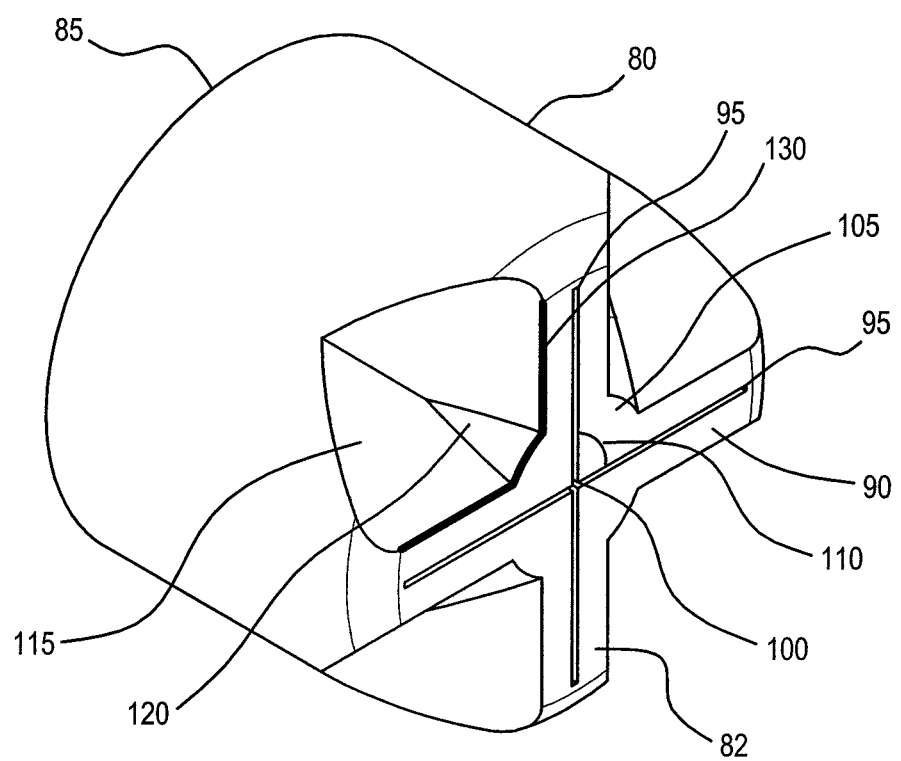
FIG. 5 is a perspective view of one embodiment of a slit valve.

Referring now to FIGS. 1, 5, 6, and 7, in one embodiment, valve assembly 35 may include a pressure-activated valve 80 having an open circular proximal end 85 and an at least partially closed distal end 90. Referring generally to FIG. 5, the distal end 90 of the valve 80 comprises at least a partially planar surface 82 having slit valves 95 oriented in different directions. The slits 95 have at least one common intersection 100 and are configured to actuate in a distal direction in response to a first pressure differential (e.g., less than or equal to approximately 2 psi). A portion 105 of the distal end 90 of the valve 80 is defined by an interior angle 110 of the at least two above-referenced slits 95. An outer portion 115 of the distal end 90 of the valve 80 tapers from the distal end 90 of the valve 80 towards the proximal end 85 of the valve 80. The tapering of the outer portion 115 of the valve 80 forms a channel 120 on the outer portion 115 of the distal end 90 of the valve 80 in the area defined by the interior angle 110 of the intersecting slits 95.

Figure 6:
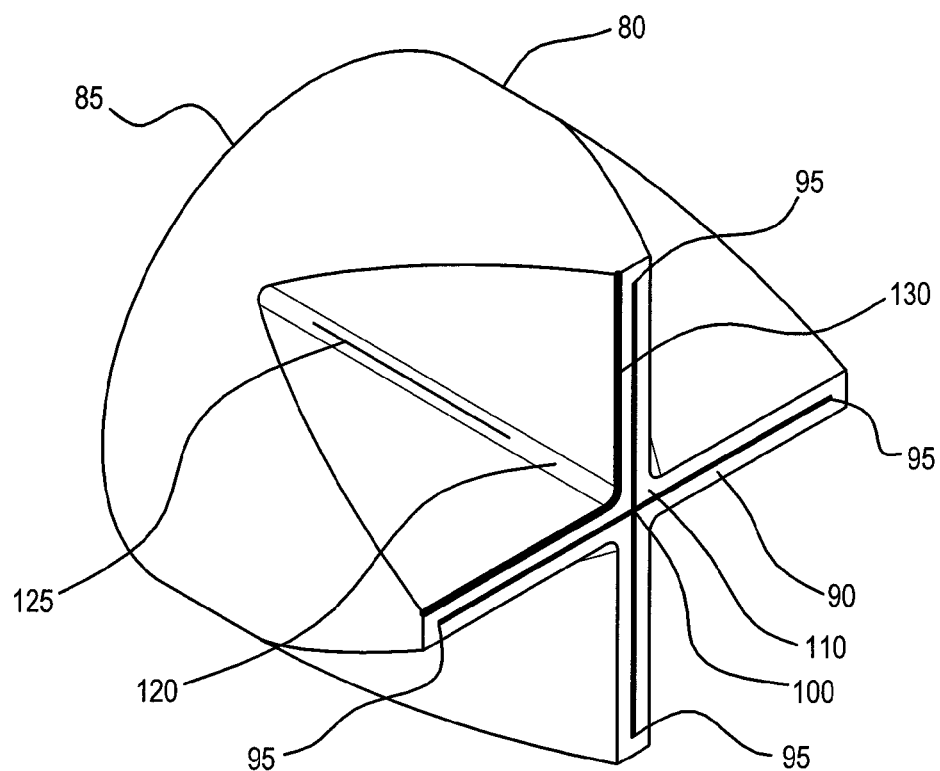
FIG. 6 is a perspective view of one embodiment of a slit valve.
Figure 7:
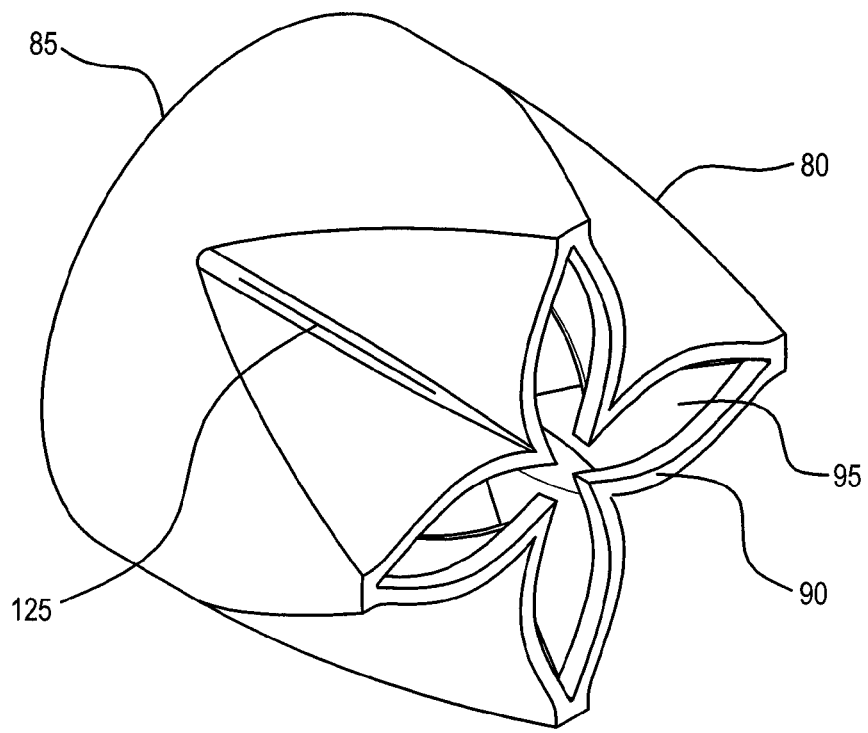
FIG. 7 is a perspective view of the slit valve of FIG. 6 in a distally open position.

As illustrated in FIG. 6, in one embodiment, at least one proximal-actuating slit valve 125 can be provided on the distal end 90 of the valve 80. The proximal-actuating slit valve 125 can be configured to actuate in a proximal direction in response to a second pressure differential (e.g., greater than or equal to approximately 2 psi), wherein the second pressure differential is greater than the first pressure differential. As depicted in FIG. 7, the infusion of fluids through the valve 80 results in deflection of the distal actuating valve 80. In one embodiment, the deflection of the valve 80 in the distal direction closes the proximal-actuating valve 125. When the pressure gradient is reversed (e.g., aspiration is underway), the proximal-actuating valve 125 is closed. In another aspect, a plurality of proximal-actuating slits 95 can be disposed on the distal end of the valve 90 oriented to approximate the shape of a cruciform. Accordingly, the distal end 90 of valve 80 is separated by the slit valves into quadrants. In one aspect of the invention, channel 120 can be formed in each quadrant of the valve 80. Moreover, the proximal-actuating slit 125 can be disposed with the channel 120 of the valve 80. In an additional embodiment, the valve 80 is configured such that the center 100 of the cruciform is approximately collinear with the center of the circular proximal end 85 of the valve 80. In an additional embodiment, the sum of the arc lengths 130 of each quadrant is equal to the circumference of the proximal end 85 of the valve 80. For example, if the arc length 130 of one quadrant is equal to 0.5 inches the circumference of the proximal end 85 of valve 80 is approximately 2 inches.

Figure 8:
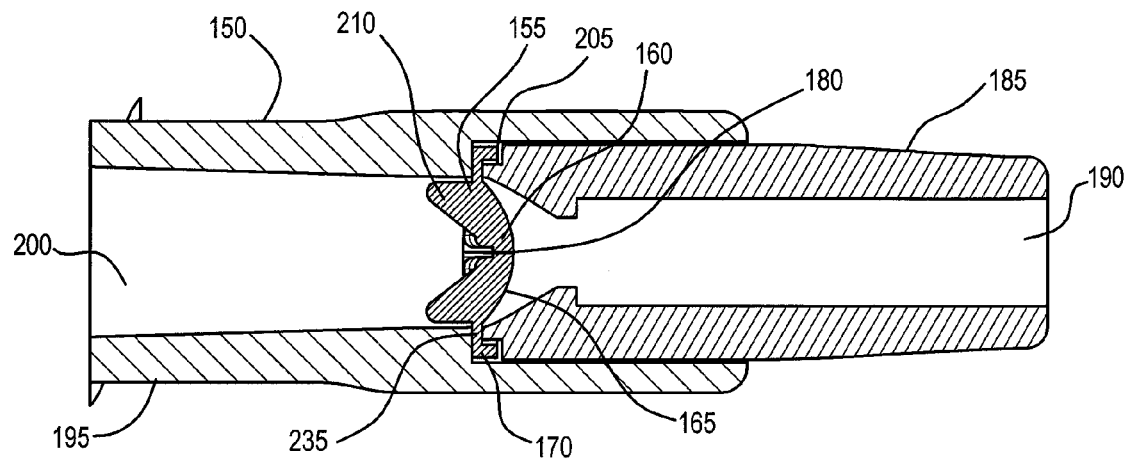
FIG. 8 is a cross section view of one embodiment of a valve assembly.
Figure 9:
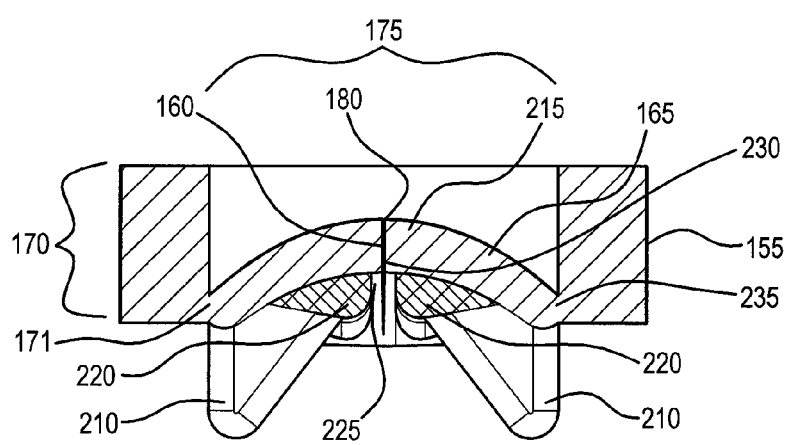
FIG. 9 is a cross section view of one embodiment of a slit valve.
Figure 10:
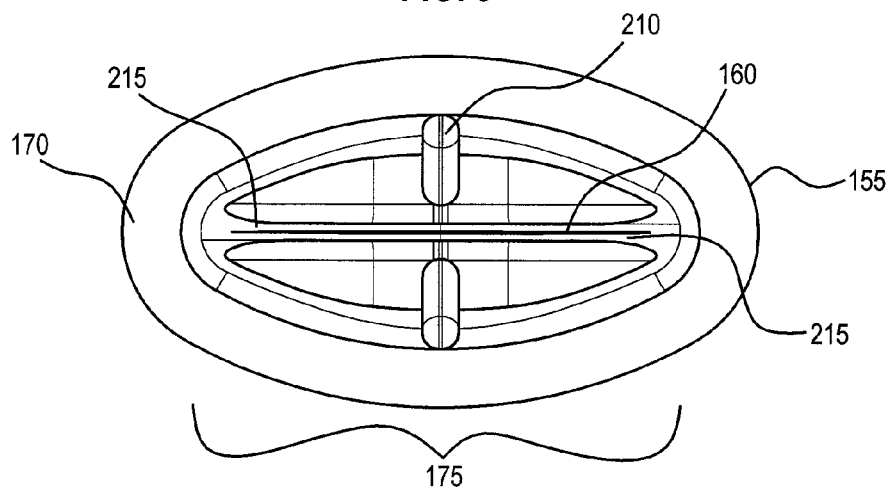
FIG. 10 is a bottom view of the slit valve of FIG. 9.

Referring now to FIGS. 8 through 10, in one embodiment, a medical device for regulating fluid flow is disclosed comprising a valve housing 150 configured to attach to a proximal end of a catheter. The medical device further comprises a diaphragm 155 with at least one bidirectional slit valve 160 disposed therein, wherein the diaphragm approximates a dome structure 165. The slit valve 160 may have linear or nonlinear orientations. The valve housing 150 is further configured to secure the diaphragm 155 at a peripheral portion 170 of the diaphragm 155. A central portion 175 of the diaphragm 155 is positioned relative to the peripheral portion 170 of the diaphragm 155 such that when the peripheral portion 170 is secured by the valve housing 150, the compressive forces acting on the peripheral portion 170 create moment forces which bias the slit valve 160 in a neutral position. Despite the moment forces which bias the slit valve 160 in a neutral position, the slit valve 160 is configured to flex in a distal direction in response to pressure (e.g., a gravity-induced liquid pressure). In one embodiment, the peripheral portion 170 of the diaphragm has a height which is at least twice the width of the hinge 171 of the diaphragm 155. In another embodiment, the height of the peripheral portion 170 is approximately twice the width of the peripheral portion. In yet another embodiment, the peripheral portion 170 is compressed by the valve housing approximately five to 15 percent. In one embodiment, the peripheral portion 170 of the diaphragm 155 has a height that ranges from approximately 0.005 inches to 0.075 inches and a thickness of the central portion 175 of the diaphragm 155 ranges from approximately 0.001 to 0.003 inches.

Referring generally to FIGS. 1 and 8 through 12, in one embodiment, the valve housing 150 comprises a distal end 185 having a central hollow portion 190 configured to connect to a proximal end of a first portion of catheter assembly 10, a distal end 20 of the first portion 15 of catheter assembly 10 is configured for placement into a vasculature of a patient 20. The valve housing 150 further comprises a proximal portion 195 having a central hollow portion 200 configured to connect to a distal end 41 of a second portion 40 of catheter 10. A proximal end 42 of the second portion 40 of catheter assembly 10 is configured to connect to a fluid source 43 and also connect to a fluid removal and fluid injection location 44. The distal portion 185 and proximal portion 195 of the valve housing 150 mate at complimentary cut-away areas 205 securing the diaphragm 155 therebetween. All or part of the peripheral portion 170 of the diaphragm 155 may be secured by the valve housing 150 depending on the desired moment forces resulting from compression of the peripheral portion 170. The distal portion 185 and proximal portion 195 of the valve housing 155 can be secured together through any suitable method (e.g., bonded or welded). In one embodiment, as illustrated in FIG. 8, the diaphragm 155 is secured such that it is perpendicular to the flow of fluid through the valve housing 150. The diaphragm 155 may be substantially circular, oval, rectangular, or any other suitable shape.

In another embodiment, the diaphragm 155 further comprises at least one arm or protrusion 210. The protrusion 210 may be placed on a proximal end of the diaphragm 155 to assist the slit valve 160 to return to a neutral position after aspiration. When the slit valve 160 opens during aspiration, the protrusion 210 contacts the valve housing 150 thereby creating a moment force opposite the direction of contact to assist the slit valve 160 to return to a neutral position after aspiration. Multiple protrusions may be added in different embodiments on both distal and/or proximal ends of the diaphragm 155 to optimize valve function.

In another embodiment, the diaphragm 155 is configured such that a portion of the proximal end of the diaphragm contiguous with the slit valve is thinner than an adjacent portion of the diaphragm. The thinner area 215 near the slit valve 160 assists in actuation of slit valve 160 as well as slit valve performance during gravity flow of fluids through the diaphragm 155. In areas where the diaphragm is thinner, the diaphragm may be reinforced as illustrated in FIG. 9. The reinforced area 220 assists in returning the slit valve 160 to a neutral position by distributing moment forces coming from protrusion 210. Additionally, the reinforced area 220 provides a secondary sealing surface 225 for an opposing valve face 230 in the event that the slit valve 160 is unable to return to a neutral position. In another aspect, the diaphragm 155 is configured such that valve hinge 171 is thinner than an adjacent portion of diaphragm 155. The thinner area near of valve hinge 171 facilitates hinge activity under lower pressures (e.g., gravity-induced pressure).

Figure 11:
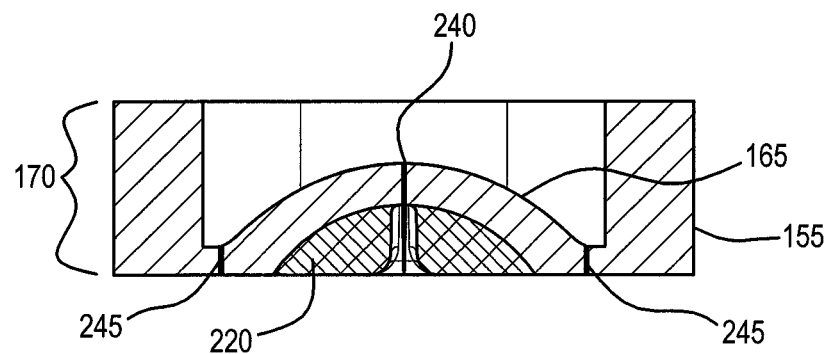
FIG. 11 is a cross section view of one embodiment of a slit valve.
Figure 12:
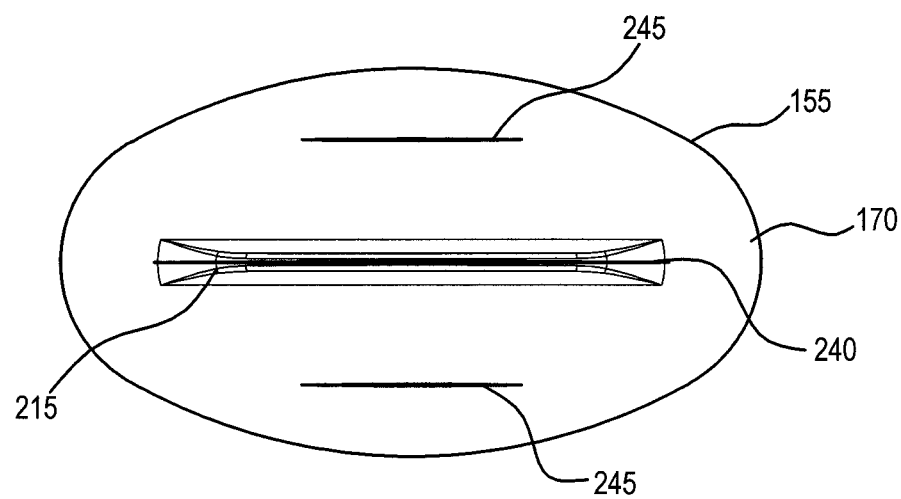
FIG. 12 is a bottom view of the slit valve of FIG. 11.

As illustrated in FIGS. 11 and 12, in one embodiment, the diaphragm 155 comprises a plurality of unidirectional slit valves. The diaphragm 155 can have a distal-actuating slit valve 240 disposed in a central region of the diaphragm 155 and at least one proximal-actuating slit valve 245 disposed on a lateral portion of the diaphragm 155. The distal-actuating slit valve 240 flexes in response to infusion-induced pressures and remains closed during aspiration. The at least one proximal-actuating slit valve 245 flexes in response to aspiration-induced pressures and remains closed during infusion procedures.

Figure 13:
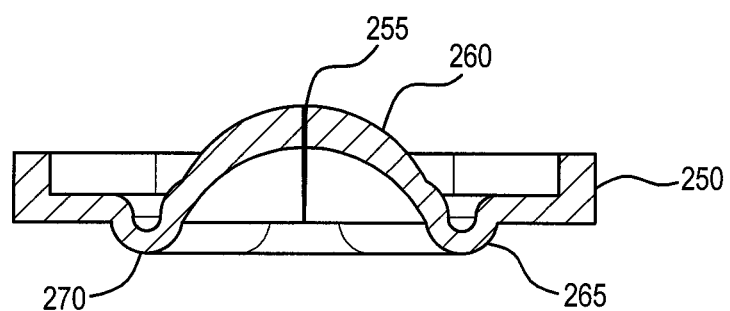
FIG. 13 is a cross section view of one embodiment of a slit valve.
Figure 14:
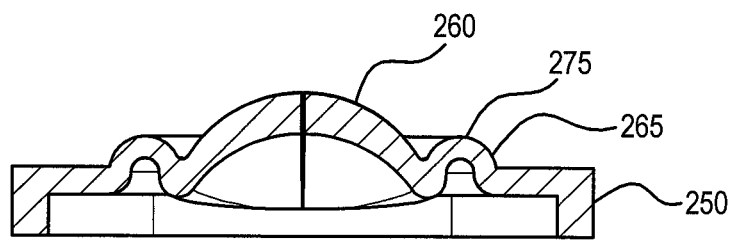
FIG. 14 is a cross section view of one embodiment of a slit valve.
Figure 15:
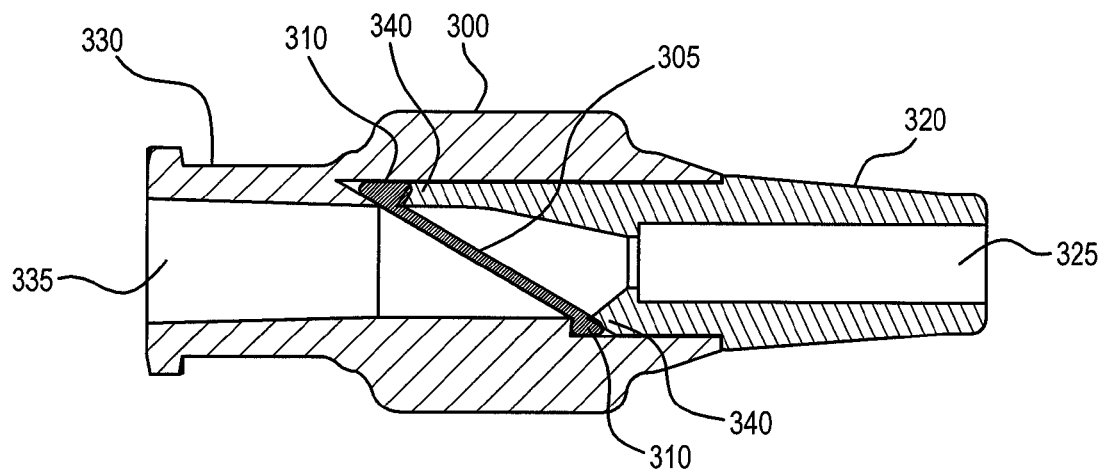
FIG. 15 is a cross section view of one embodiment of a valve assembly.
Figure 16:
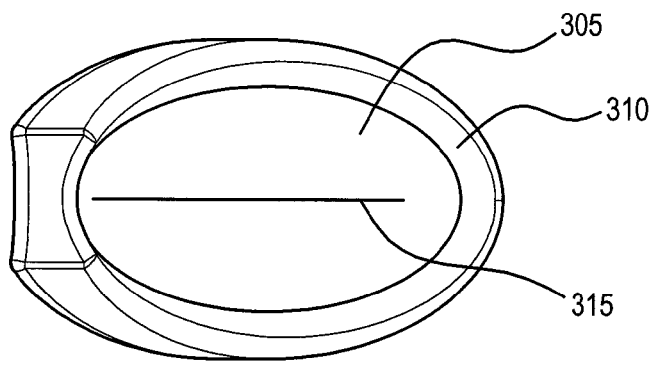
FIG. 16 is a top view of one embodiment of a slit valve.
Figure 17:
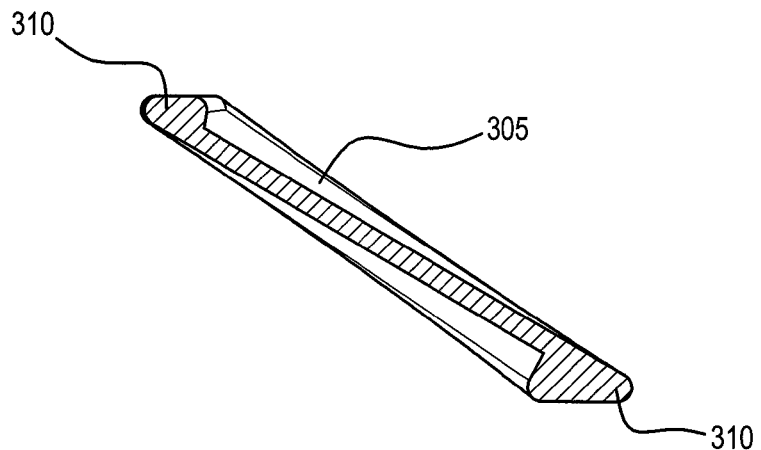
FIG. 17 is a cross section view of the slit valve of FIG. 16.

Referring to FIGS. 13 and 14, in one embodiment of the present invention, a diaphragm 250 is disclosed having at least one bidirectional slit valve 255 disposed therein. The diaphragm 250 approximates a dome structure 260. The diaphragm 250 further comprises an annular member 265 which circumscribes the dome structure 260. In one embodiment, the annular member 265 is oriented with its apex 270 in a proximal direction. In another embodiment, the annular member 265 is oriented with its apex 275 in a distal direction.

Referring now to FIGS. 1 and 15 through 17, in one embodiment, a valve assembly is disclosed comprising a valve housing 300 configured to secure a diaphragm 305 at a peripheral portion 310 of the diaphragm 305. The diaphragm 305 has at least one slit valve 315 disposed therein and is oriented within the valve housing 300 at a direction which is at an obtuse angle relative to the direction of fluid flow through the valve housing 300. The valve housing 300 comprises a distal end 320 having a central hollow portion 325 configured to connect to a proximal end 30 of a first portion 15 of catheter assembly 10. A distal end 20 of the first portion 15 of catheter assembly 10 is configured for placement into a vasculature 12 of patient 25. The valve housing 300 further comprises a proximal portion 330 having a central hollow portion 335 configured to connect to a distal end 41 of a second portion 40 of catheter assembly 10. A proximal end 42 of the second portion 40 of catheter assembly 10 is configured to connect to a fluid source 43 and also connect to a fluid removal and fluid injection location 44. The distal portion 320 and proximal portion 330 of the valve housing 300 mate at complimentary cut-away areas 340 securing the diaphragm 305 therebetween. All or part of the peripheral portion 310 of the diaphragm 305 may be secured by the valve housing 300 depending on the desired moment forces resulting from compression of the peripheral portion 310. The diaphragm 305 can have a substantially circular shape, a substantially oval shape, a substantially rectangular shape, or any other suitable shape, and can also approximate a dome structure. The distal portion 320 and proximal portion 330 of the valve housing 300 can be secured together through any suitable method (e.g., bonded or welded). In another embodiment, the surface area of diaphragm 305 subjected to pressure actuation (e.g., not in contact with any portion of the valve housing 300) is greater on a proximal end of the diaphragm 305 than a distal end of the diaphragm 305. The amount of the slit valve 315 disposed in diaphragm 305 that is subject to pressure actuation (e.g., not in contact with any portion of the valve housing 300) is equal on both distal and proximal ends of the diaphragm 305. This can be accomplished by varying the shape or size of the distal portion 320 and proximal portion 330 of valve housing 300.

Figure 18:
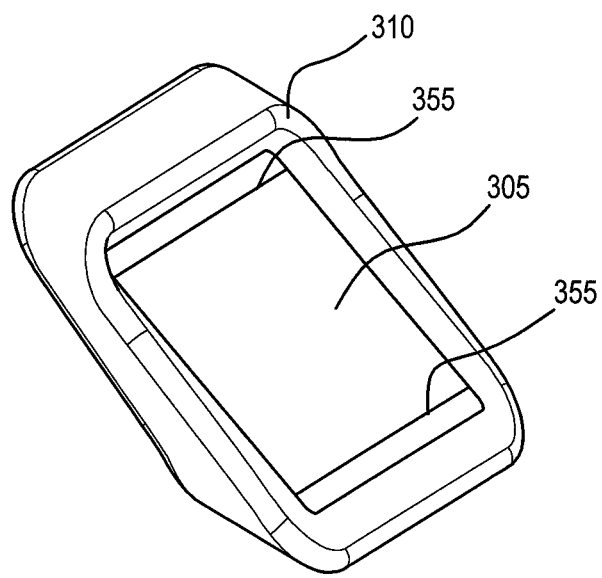
FIG. 18 is a perspective view of one embodiment of a slit valve.
Figure 19:
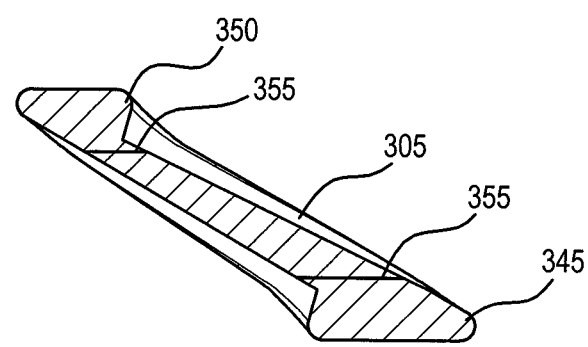
FIG. 19 is a cross section view of the slit valve of FIG. 18.

Referring now to FIGS. 18 and 19, in an additional embodiment, the diaphragm narrows from a lateral portion 345 of the diaphragm 305 to an opposite lateral portion 350 of the diaphragm 305. In another embodiment, the diaphragm 305 has two slit valves 355 disposed on opposing sides of the diaphragm 305. Each slit valve 355 is unidirectional. A first valve is configured to actuate in a distal direction in response to an infusion-induced pressure differential. A second valve is configured to actuate in a proximal direction in response to an aspiration-induced pressure differential. The relative thickness of lateral portions of diaphragm 305 control the actuation pressure of the slit valves 355.

Figure 20:
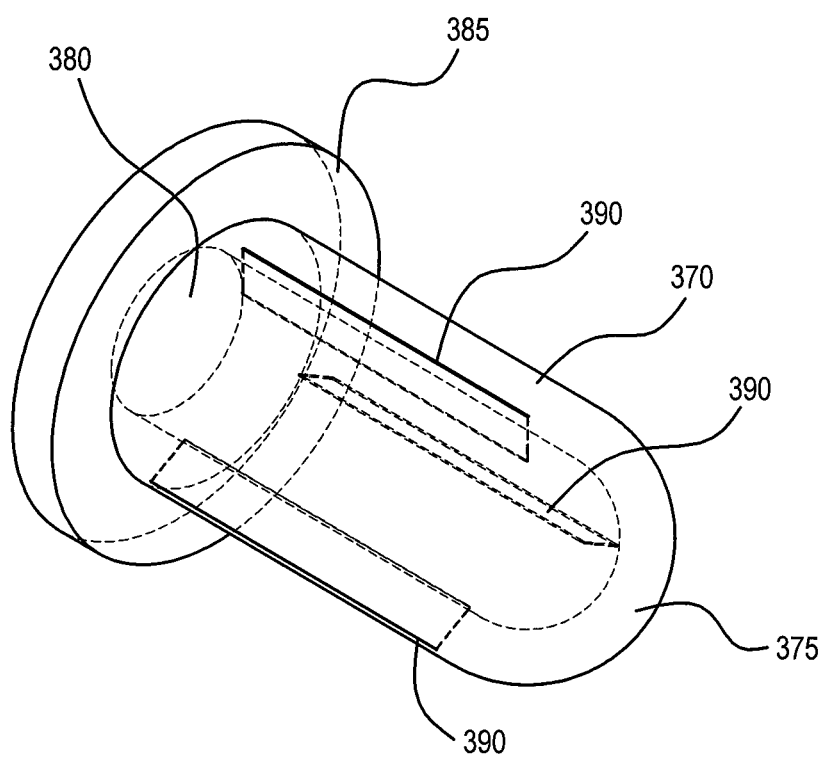
FIG. 20 is a perspective view of one embodiment of a slit valve.

Referring now to FIG. 20, in an additional aspect, a medical device for regulating fluid flow is disclosed comprising a generally cylindrical member 370 having a closed distal end 375 and an open proximal end 380. The proximal end 380 further comprises a shoulder member 385 configured to be secured at least partially by a valve housing. The cylindrical member 370 has at least one slit valve 390 disposed therein being oriented parallel to a longitudinal axis of the cylindrical member 370. In another aspect, the cylindrical member 370 further comprises a plurality of slit valves 390 disposed on the cylindrical member 370.

Figure 21:
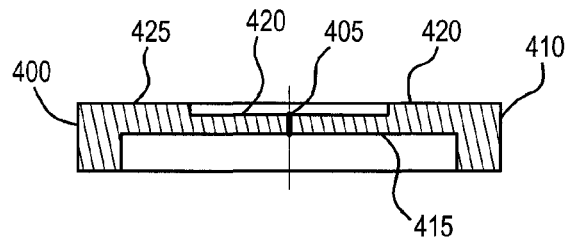
FIG. 21 is cross section view of one embodiment of a slit valve.
Figure 22:
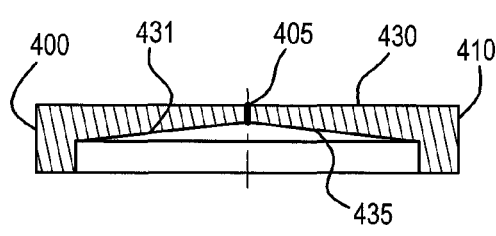
FIG. 22 is a cross section view of one embodiment of a slit valve.
Figure 23:
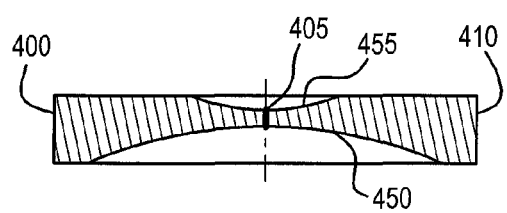
FIG. 23 is cross section view of one embodiment of a slit valve.
Figure 24:
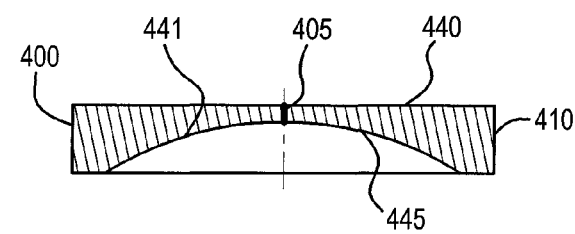
FIG. 24 is a cross section view of one embodiment of a slit valve.
Figure 25:
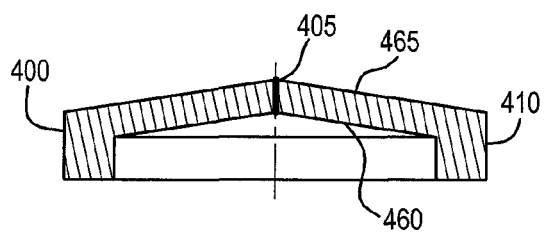
FIG. 25 is cross section view of one embodiment of a slit valve.
Figure 26:
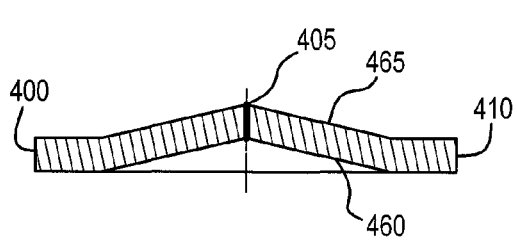
FIG. 26 is a cross section view of one embodiment of a slit valve.

Referring generally to FIGS. 21 and 22, a diaphragm 400 for regulating fluid flow is disclosed having at least one slit valve 405 disposed therein. The diaphragm 400 can be secured in a valve housing at a peripheral portion 410 of the diaphragm. In this embodiment, a proximal surface 415 of the diaphragm 400 is substantially planar. Likewise, a distal surface 420 of the diaphragm 400 is substantially planar. A central portion 420 of the diaphragm 400 is thinner than an outer region 425 of the diaphragm 400. In another embodiment, the distal surface 430 of the diaphragm 400 is substantially planar and the proximal surface is substantially conical 435. In another embodiment, referring generally to FIGS. 23 and 24, the proximal surface 440 of the diaphragm 400 is substantially planar and the distal surface of the diaphragm 400 approximates a spherical cap 445. In another embodiment, the distal surface 450 of the diaphragm 400 approximates a spherical cap and the proximal surface 455 of the diaphragm 400 also approximates a spherical cap. The virtual centers of the opposing spherical caps of the diaphragm 400 can be collinear. The spherical cap on the distal surface 455 can be smaller than the spherical cap on the proximal surface 450. In yet another embodiment, referring generally to FIGS. 25 and 26, a proximal surface 460 of the diaphragm 400 is substantially conical. The distal surface 465 of the diaphragm 400 is also substantially conical.

The diaphragms discussed herein can be molded in one piece from an elastomeric material (e.g., a silicone rubber having a Shore A Durometer rating from about 30 to 60). It should be noted that any of the diaphragms discussed herein can be manufactured from any elastomeric material including, without limitation, polyisoprene, butyl rubber, halogenated butyl rubbers, polybutadiene, styrene-butadiene rubber, nitrile rubber, hydrated nitrile rubbers, Therban® elastomer, Zetpol® elastomer, chloroprene rubber, polychloroprene, neoprene, baypren, EPM (ethylene propylene rubber, a copolymer faeces of polyethylene and polypropylene), EPDM rubber (ethylene propylene diene rubber, a terpolymer of polyethylene, polypropylene and a diene-component), epichlorohydrin rubber, polyacrylic rubber, fluorosilicone rubber, fluoroelastomers, Viton® elastomer, Tecnoflon® elastomer, Fluorel® elastomer, Dai-El® elastomer, perfluoroelastomers, tetrafluoro ethylene/propylene rubbers, chlorosulfonated polyethylene, Hypalon® elastomer, ethylene-vinyl acetate, Hytrel® elastomer, Santoprene® elastomer, polyurethane rubber, resilin, elastin, and/or Polysulfide rubber.

The valve housings discussed herein can be molded in one or more pieces from a thermoplastic material (e.g., a polyethylene terephthalate having a Shore A Durometer rating from about 60 to 85). It should be noted that any of the valve housings discussed herein can be manufactured from any thermoplastic material including, without limitation, acrylonitrile butadiene styrene, acrylic, celluloid, cellulose acetate, ethylene-vinyl acetate, ethylene vinyl alcohol, fluoroplastics, ionomers, polyacetal, polyacrylates, polyacrylonitrile, polyamide, polyamide-imide polyaryletherketone, polybutadiene, polybutylene, polybutylene terephthalate, polyethylene terephthalate, polycyclohexylene dimethylene terephthalate, polycarbonate, polyhydroxyalkanoates, polyketone, polyester, polyethylene, polyetheretherketone, polyetherimide, polyethersulfone, polyethylenechlorinates, polyimide, polylactic acid, polymethylpentene, polyphenylene oxide, polyphenylene sulfide, polyphthalamide, polypropylene, polystyrene, polysulfone, and/or polyvinyl chloride.

Any of the catheters described herein can be manufactured from any biocompatible material suitable for placement into a portion of a patient.

Although the above-described embodiments show a particular configuration of a pressure-actuated valve and valve assembly, such embodiments are exemplary. Accordingly, many different embodiments are contemplated and encompassed by this disclosure. It should also be understood that the device and method for controlling fluid flow through a catheter can be used with any method or device wherein fluids are administered to or removed from a patient.

While certain embodiments and details have been included herein for purposes of illustrating aspects of the instant disclosure, it will be apparent to those skilled in the art that various changes in the systems, apparatuses, and methods disclosed herein may be made without departing from the scope of the instant disclosure, which is defined, in part, in the appended claims. The words "including" and "having," as used herein including the claims, shall have the same meaning as the word "comprising."

What is claimed is:

1. A pressure-activated valve for regulating fluid flow through a catheter comprising:
 a valve for selectively accommodating flow of liquid through the catheter, the flow of a first liquid passing in one direction through a central slit in response to a first pressure differential and the flow of a second liquid in an opposite second direction through a first lateral slit in response to a second pressure differential, the second liquid including at least one body fluid, the valve including a dome-shaped portion having the central slit disposed thereon, a first lateral region adjacent a first side of the dome-shaped portion having the first lateral slit disposed thereon, and a peripheral portion; and
 a valve housing configured to secure the peripheral portion of the valve.

2. The medical device of claim 1, wherein a second lateral slit is disposed on a second lateral region of the valve adjacent a second side of the dome-shaped portion.

3. The medical device of claim 2, wherein the central slit, first lateral slit, and second lateral slit are substantially parallel to one another.

4. A medical system comprising:
a medical device configured to infuse a first fluid into a patient's body and to aspirate a second fluid from the patient's body;
a diaphragm having at least two unidirectional slit valves disposed therein, including a first unidirectional slit valve that is structurally configured to actuate to allow flow of the first fluid through the medical device in a distal direction in response to infusion-induced pressures and to remain closed when subjected to aspiration-induced pressures, and a second unidirectional slit valve that is structurally configured to actuate to allow flow of the second fluid through the medical device in a proximal direction in response to aspiration-induced pressures and to remain closed when subjected to infusion-induced pressures; and
a valve housing securing the diaphragm at a peripheral portion of the diaphragm.

5. The medical system of claim 4, wherein the first unidirectional slit valve is located in a center of the diaphragm, and the second unidirectional slit valve is adjacent the peripheral portion of the diaphragm.

6. The medical system of claim 4, wherein the diaphragm also includes a third unidirectional slit valve that is configured to actuate only in a proximal direction in response to aspiration-induced pressures and to remain closed when subjected to infusion-induced pressures, wherein the third unidirectional slit valve is separated from the first unidirectional slit valve and the second unidirectional slit valve.

7. The medical system of claim 6, wherein the first unidirectional slit valve, the second unidirectional slit valve, and the third unidirectional slit valve are substantially parallel to one another.

8. The medical system of claim 4, wherein the diaphragm comprises a generally dome-shaped portion and an annular peripheral portion.

9. The medical system of claim 8, wherein the generally dome-shaped portion does not collapse when subjected to aspiration-induced pressures.

10. The medical system of claim 4, wherein a central portion of the diaphragm is positioned relative to the peripheral portion of the diaphragm such that when the peripheral portion is secured by the valve housing, compressive forces acting on the peripheral portion of the diaphragm create moment forces which bias the first unidirectional slit valve in a neutral position.

11. The medical system of claim 4, wherein the first unidirectional slit valve actuates at a first infusion-induced pressure and the second unidirectional slit valve actuates at a second aspiration-induced pressure that is greater than the infusion-induced pressure.

12. The medical system of claim 11, wherein the first unidirectional slit valve actuates at the first infusion-induced pressure that is less than approximately 2 psi and the second unidirectional slit valve actuates at the second aspiration-induced pressure that is greater than approximately 2 psi.

13. The medical system of claim 4, wherein the first unidirectional slit valve and the second unidirectional slit valve are not contiguous.

14. The medical system of claim 4, wherein the diaphragm comprises a generally dome-shaped portion and a lateral region located between the generally dome-shaped portion and the peripheral portion of the diaphragm secured by the valve housing, the first unidirectional slit valve located in the generally dome-shaped portion, and the second unidirectional slit valve located in the lateral region.

15. The medical system of claim 4, wherein an outer portion of the diaphragm has a first thickness that is different from a second thickness of an inner portion of the diaphragm.

16. The medical system of claim 4, wherein an outer portion of the diaphragm is thicker than an inner portion of the diaphragm.

17. The medical system of claim 4, wherein the diaphragm further comprises a reinforced area.

18. The medical system of claim 4, wherein the diaphragm further comprises at least one slit valve secondary sealing surface.

19. The medical system of claim 4, wherein a surface area of a proximal portion of the diaphragm subject to fluid pressure is greater than a surface area of a distal portion of the diaphragm subject to fluid pressure.

20. A medical device comprising:
a catheter configured to infuse a first liquid into a patient's body and to aspirate a second liquid from the patient's body;
a diaphragm having at least two unidirectional slit valves disposed therein, including a first unidirectional slit valve that actuates to allow liquid to flow from a proximal end to a distal end of the catheter at a first liquid-induced pressure, and a second unidirectional slit valve that actuates to allow liquid to flow from the distal end to the proximal end of the catheter at a second liquid-induced pressure different from the first liquid-induced pressure, wherein the second unidirectional slit valve is separated from the first unidirectional slit valve; and
a valve housing securing the diaphragm at a peripheral portion of the diaphragm.

* * * * *